United States Patent
Xu et al.

(10) Patent No.: US 11,896,433 B2
(45) Date of Patent: Feb. 13, 2024

(54) ULTRASOUND DETERMINATION OF DYNAMIC AIR BRONCHOGRAM AND ASSOCIATED DEVICES, SYSTEMS, AND METHODS

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Shougang Wang, Ossining, NY (US); Anthony M. Gades, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 848 days.

(21) Appl. No.: 16/638,827

(22) PCT Filed: Aug. 16, 2018

(86) PCT No.: PCT/EP2018/072256
§ 371 (c)(1),
(2) Date: Feb. 13, 2020

(87) PCT Pub. No.: WO2019/034743
PCT Pub. Date: Feb. 21, 2019

(65) Prior Publication Data
US 2021/0128116 A1    May 6, 2021

Related U.S. Application Data

(60) Provisional application No. 62/628,361, filed on Feb. 9, 2018.

(30) Foreign Application Priority Data

Aug. 16, 2017  (WO) ................ PCT/CN2017/097624

(51) Int. Cl.
*A61B 8/08*     (2006.01)
*G06T 7/00*     (2017.01)
(Continued)

(52) U.S. Cl.
CPC ............... *A61B 8/5223* (2013.01); *A61B 8/08* (2013.01); *G06T 7/0016* (2013.01);
(Continued)

(58) Field of Classification Search
CPC ....... A61B 8/5223; A61B 8/08; A61B 8/0858; A61B 8/461; A61B 8/5246; G06T 7/0016;
(Continued)

(56) References Cited

U.S. PATENT DOCUMENTS

| | | |
|---|---|---|
| 2013/0197370 A1 | 8/2013 | Burlina et al. |
| 2015/0002538 A1 | 1/2015 | Sohn et al. |
| 2015/0150503 A1 | 6/2015 | Pamnani et al. |

FOREIGN PATENT DOCUMENTS

| | | |
|---|---|---|
| WO | 2014195742 A1 | 12/2014 |
| WO | 2016046140 A1 | 3/2016 |
| WO | 2017046692 A1 | 3/2017 |

OTHER PUBLICATIONS

Lichtenstein et al.; The Dynamic Air Bronchogram: A Lung Ultrasound Sign of Alveolar Consolidation Ruling Out Atelectasis; published in Jun. 2009; Chest, vol. 135, Issue 6, 2009, pp. 1421-1425 (Year: 2009).*

(Continued)

*Primary Examiner* — Chao Sheng

(57) ABSTRACT

Ultrasound image devices, systems, and methods are provided. In one embodiment, an ultrasound imaging system includes an interface coupled to an ultrasound imaging component and configured to receive a plurality of image data frames representative of a subject's body including at (Continued)

least a portion of a lung; a processing component in communication with the interface and configured to determine a metric for each image data frame of the plurality of image data frames based on a threshold comparison; and determine a dynamic air bronchogram (AB) condition of the subject's body based on a variation across the metrics of the plurality of image data frames. In one embodiment, the processing component is configured to determine differential data frames based on differences across consecutive image data frames of the plurality of image data frames; and determine a dynamic AB condition of the subject's body based on the differential data frames.

10 Claims, 12 Drawing Sheets

(51) Int. Cl.
*A61B 8/00* (2006.01)
*G01S 7/52* (2006.01)
(52) U.S. Cl.
CPC .............. *A61B 8/0858* (2013.01); *A61B 8/461* (2013.01); *A61B 8/5246* (2013.01); *G01S 7/5208* (2013.01); *G06T 2207/10016* (2013.01); *G06T 2207/10132* (2013.01); *G06T 2207/20212* (2013.01); *G06T 2207/30061* (2013.01)
(58) Field of Classification Search
CPC . G06T 2207/10016; G06T 2207/10132; G06T 2207/20212; G06T 2207/30061; G01S 7/5208
See application file for complete search history.

(56) References Cited

OTHER PUBLICATIONS

Mahabadi et al. Anatomy, Thorax, Lung Pleura And Mediastinum. [Updated Oct. 17, 2022]. In: StatPearls [Internet]. Treasure Island (FL): StatPearls Publishing; Jan. 2022-. Available from: https://www.ncbi.nlm.nih.gov/books/NBK519048/ (Year: 2022).*

Barrientos et al: "Automatic Detection of Pneumonia Analyzing Ultrasound Digital Images"; 2016 IEEE 36TH Central American and Panama Convention, Nov. 2016, pp. 1-4.

Cisneros-Velarde et al: "Automatic Pneumonia Detection Based On Ultrasound Video Analysis"; 2016 38th Annual International Conference of the IEEE Engineering in Medicine ANDB Biology Society, Aug. 2016, pp. 4117-4120.

Weinberg et al: "The Air Bronchogram:Sonographic Demonstration"; AJR, vol. 147, pp. 593-595.

Volpicelli et al: "Usefulness of Lung Ultrasound in the Bedside Distinction Between Pulmonary Edema and Exacerbation of COPD"; Emerg Radiol (2008), vol. 15, pp. 145-151.

Wikipedia: "Pneumonia", Background Information On Pneumonia, 31 Page Document.

PCT/EP2018/077256 Written Opinion and ISR, Oct. 31, 2018, 19 Page Document.

Perera et al: "The Rush Exam:Rapid Ultrasound in Shock in the Evaluation of the Critically Ill";Emerg Med Clin Na Am (2010), pp. 29-56.

Lichtenstein et al: "The Dynamic Air Bronchogram"; Chest Journal, Jun. 2009, vol. 135, Issue 6, pp. 1421-1425.

Georgopoulos et al: "Lung Ultrasound in the Intensive Care Unit: Let's Move Forward"; Intensive Care Med (2014), vol. 40, pp. 1592-1594.

Ellington et al: "Computerised Lung Sound Analysis To Improve the Specificity of Paediatric Pneumonia Diagnosis in Resource-Poor Settings:Protocol and Methods for an Observational Study"; BMJ Open, 2012, vol. 2:e000506, pp. 1-7.

Corradi et al: "Quatitative Analysis of Lung Ultrasonography for the Detection of Community-Acquired Pneumonia:A Pilot Study"; Hindawi Publishing Corporation, Biomed Research International, vol. 2015, Article ID 868707, 2015, 8 Pages.

Chavez et al:"LUNG Ultrasound for the Diagnosis of Pneumonia in Adults:A Systematic Review and Meta-Analysis"; Respiratory Research, Article No. 50, Apr. 2014, 13 Page Article.

Blaivas: "Lung Ultrasound in Evalutation of Pneumonia"; J. Ultrasound Med 2012, vol. 31, pp. 823-826.

* cited by examiner

ULTRASOUND DETERMINATION OF DYNAMIC AIR BRONCHOGRAM AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2018/072256, filed on Aug. 16, 2018, which claims the benefit of U.S. Provisional Patent Application No. 62/628,361 filed on Feb. 9, 2018 and CN Patent Application No. PCT/CN2017/097624, filed on Aug. 16, 2017. These applications are hereby incorporated by reference herein.

TECHNICAL FIELD

The present disclosure relates generally to ultrasound imaging and, in particular, to providing automated systems and methods for identifying the presence of a dynamic air bronchogram (AB) indicative of pneumonia based on lung ultrasound imaging.

BACKGROUND

Pneumonia (PN) is a common disease worldwide, with about 2 million to about 3 million cases diagnosed annually in the United States. The symptoms of PN may include high fever, cough, shortness of breath, chest pain, and/or other respiratory-related symptoms. Physical examinations (e.g., listening to an area over the chest for lung sounds) may not be effective or reliable for detection of PN at an early stage. One of the commonly used techniques for PN diagnosis is chest radiography (CXR). However, bedside CXR may provide limited image quality. In addition, CXR is a time-consuming procedure for emergency situations and the interpretation of bedside CXR may be challenging, requiring extensive radiologic experience to avoid misinterpretation of the wide spectrum of pleural and pulmonary diseases. Further, final results may have a high variability among radiologists. An improved approach to diagnosing PN compared to bedside CXR is to use thoracic computerized tomography (CT) imaging. However, CT imaging can be expensive and may have a higher radiation exposure than CXR. Thus, CT imaging may not be suitable for routine-diagnostics in emergency department, critical care units (CCUs), or intensive care units (ICUs), especially for young children and pregnant women.

Ultrasound imaging, especially point-of-care ultrasound (POC-US) at bedside, has gain popularity ICUs and emergency situations for various types of diagnostics. Recent studies have shown that lung ultrasound imaging can be useful and effective in diagnosis of PN with a relatively high accuracy. For example, ultrasound images may not show useful or adequate information for a normal aerated lung, whereas a lung consolidation may appear as bright spots or bright structures under ultrasound imaging. In addition, the appearance of brightness (B)-lines in ultrasound images may be indicative of PN at an early stage. Thus, POC lung ultrasound imaging can be useful and attractive for PN diagnosis. However, ultrasound imaging-based PN diagnosis may require a well-trained or experienced physician or clinician to analyze and interpret acquired lung image. Currently, there is no effective tool in guiding inexperience users for screening and diagnosis of PN.

SUMMARY

While existing ultrasound lung imaging has proved useful for diagnosis of PN, there remains a clinical need for improved systems and techniques for providing low-cost and easily interpreted PN diagnostic results. Embodiments of the present disclosure provide mechanisms for diagnosing PN by identifying and indicating the presence of a dynamic air bronchogram (AB) based on lung ultrasound images in an automated manner. Under lung ultrasound imaging, dynamic ABs correspond to bright spots or pixels that change or move over time due to respiratory cycles. In one embodiment, dynamic AB is identified based on a variation of a number of bright spots or pixels across a number of image frames over time. In another embodiment, dynamic AB is identified based on a temporal intensity variation of bright spots or pixels across a number of image frames over time. In yet another embodiment, the appearance of bronchial trees corresponding to dynamic ABs are enhanced in lung ultrasound images by accumulating differences across image data frames over time.

In one embodiment, an ultrasound imaging system is provided. The ultrasound imaging system includes an interface coupled to an ultrasound imaging component and configured to receive a plurality of image data frames representative of a subject's body including at least a portion of a lung; a processing component in communication with the interface and configured to determine a metric for each image data frame of the plurality of image data frames based on a threshold comparison; and determine a dynamic air bronchogram (AB) condition of the subject's body based on a variation across the metrics of the plurality of image data frames.

In some embodiments, each image data frame includes a plurality of pixel values representing pixel intensities of an image of the subject's body. In some embodiments, the plurality of image data frames represent images of the subject's body across a time period including at least one respiratory cycle. In some embodiments, the processing component is configured to determine the metric for each image data frame of the plurality of image data frames by determining a number of the plurality of pixel values in each image data frame that satisfies a threshold. In some embodiments, the processing component is configured to determine the dynamic AB condition by determining a ratio between a maximum of the metrics and a minimum of the metrics; and determining the dynamic AB condition based on the ratio. In some embodiments, the processing component is further configured to identify a region-of-interest (ROI) from the plurality of image data frames corresponding to the at least a portion of the lung; and determine the metrics based on the ROI. In some embodiments, the ultrasound imaging system further includes a display component configured to display a result of the dynamic AB condition. In some embodiments, the ultrasound imaging system further includes an ultrasound imaging probe including the ultrasound imaging component; the processing component; and a display component configured to display a result of the dynamic AB condition.

In one embodiment, an ultrasound imaging system is provided. The ultrasound imaging system includes an interface coupled to an ultrasound imaging component and configured to receive a plurality of image data frames representative of a subject's body including at least a portion of a lung; a processing component in communication with the interface and configured to determine differential data frames based on differences across consecutive image data frames of the plurality of image data frames; determine an accumulated data frame based on a sum of the differential data frames; and determine a dynamic air bronchogram (AB) condition of the subject's body based on the accumulated data frame.

In some embodiments, the plurality of image data frames represent images of the subject's body across a time period including at least one respiratory cycle. In some embodiments each image data frame includes a plurality of pixel values representing pixel intensities of an image of the subject's body. In some embodiments, each differential data frame includes a plurality of difference values, wherein the processing component is further configured to determine each differential data frame by determining each difference value of the plurality of difference values by determining an absolute difference between a pixel value of a first data frame of the plurality of image data frames and a pixel value of a second data frame of the plurality of image data frames, wherein the first data frame is adjacent to the second data frame, and wherein the pixel value of the first data frame and the pixel value of the second data frame represents a same sub-portion of the at least a portion of the lung. In some embodiments, each differential data frame includes a first plurality of pixel values, wherein the accumulated data frame includes a plurality of sum values, and wherein the processing component is further configured to determine the dynamic AB condition by determining each sum value of the plurality of sum values by accumulating a second plurality of pixel values across the differential data frames, wherein the second plurality of pixel values across the differential data frames represent a same portion of the subject's body; and determining the dynamic AB condition based on the plurality of sum values. In some embodiments, the ultrasound imaging system of claim 9, further comprising a display component configured to display the accumulated data frame.

In one embodiment, an ultrasound imaging system is provided. The ultrasound imaging system includes an interface coupled to an ultrasound imaging component and configured to receive a plurality of image data frames representative of a subject's body including at least a portion of a lung; a processing component in communication with the interface and configured to identify a subset of data from the plurality of image data frames based on a threshold comparison; and determine a dynamic air bronchogram (AB) condition of the subject's body based on a temporal variation across the subset of data.

In some embodiments, each image data frame of the plurality of image data frames includes a plurality of pixel values representing pixel intensities of an image of the subject's body. In some embodiments, the plurality of image data frames represent images of the subject's body across a time period including at least one respiratory cycle. In some embodiments, the processing component is configured to identify the subset of data by selecting one or more pixel values from each image data frame of the plurality of image data frames corresponding to a same sub-portion of the at least a portion of the lung and satisfying a threshold; determine a first value for each image data frame of the plurality of image data frames based on the one or more pixel values of a corresponding image data frame; and determine the dynamic AB condition based on a ratio between a maximum of the first values and a minimum of the first values. In some embodiments, the processing component is configured to apply a filter across the first values prior to the determining the dynamic AB condition. In some embodiments, the ultrasound imaging system further includes a display component configured to display a result of the dynamic AB condition.

In one embodiment, a method of ultrasound imaging diagnostic is provided. The method includes receiving, from an ultrasound imaging probe, a plurality of image data frames associated with a subject's body including at least a portion of a lung; determining a first value for each image data frame of the plurality of image data frames based on a threshold comparison; and determine a dynamic air bronchogram (AB) condition of the subject's body based on a variation across the first values of the plurality of image data frames.

In some embodiments, each image data frame includes a plurality of pixel values representing pixel intensities of an image of the subject's body. In some embodiments, the plurality of image data frames represents images of the subject's body across a time period including at least one respiratory cycle. In some embodiments, the determining the first value includes determining a number of the plurality of pixel values in each image data frame that satisfies a threshold, and wherein the determining the dynamic AB condition includes determining a ratio between a maximum of the first values and a minimum of the first values; and determining the dynamic AB condition based on the ratio. In some embodiments, the method further includes identifying a region of interest (ROI) from the plurality of image data frames corresponding to the at least a portion of the lung; and determining the first values based on the ROI. In some embodiments, the method further includes displaying, at a display component, a result of the dynamic AB condition.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
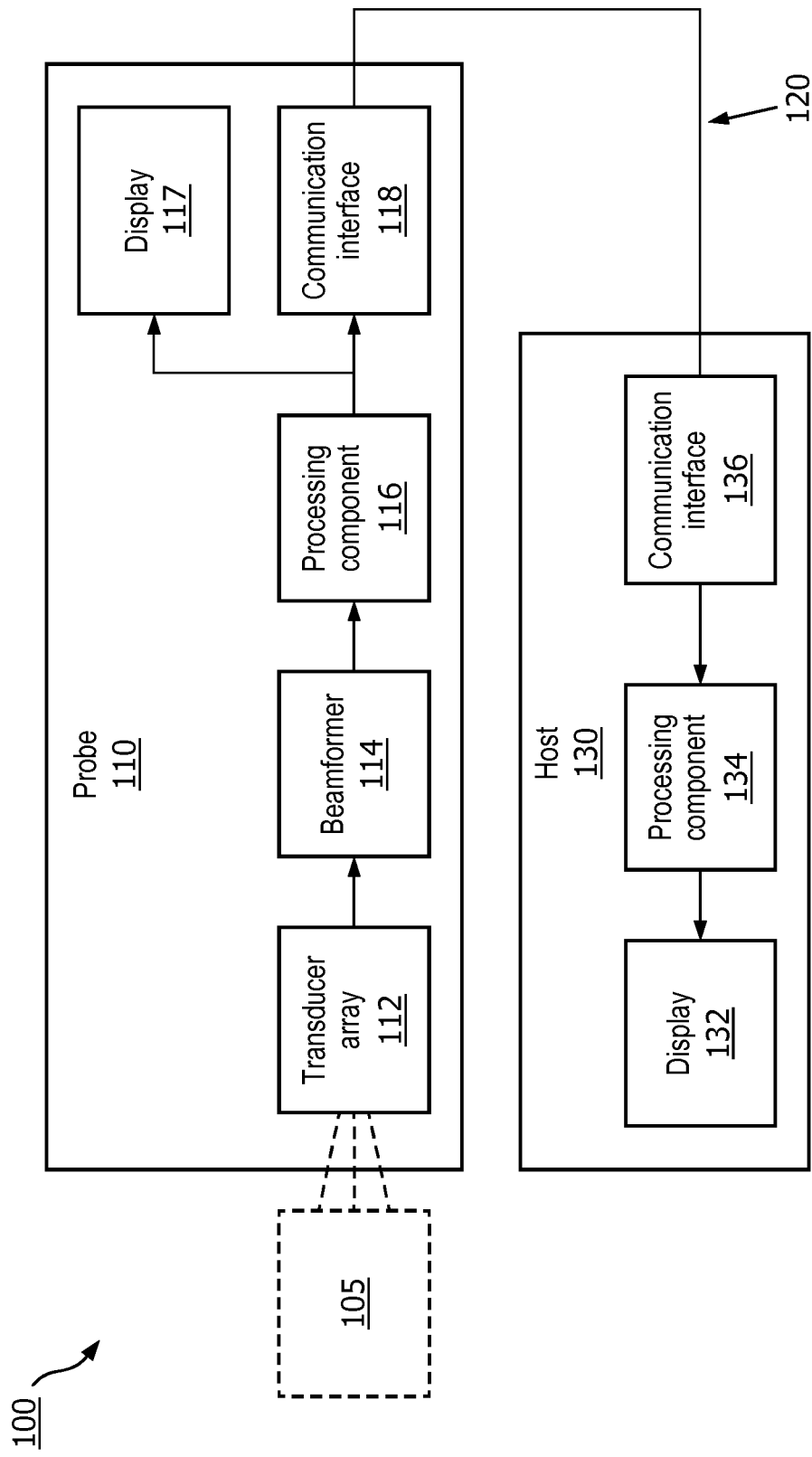
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, a display 117, and a communication interface 118. The host 130 includes a display 132, a communication interface 136, and a communication interface 136.

The transducer array 112 emits ultrasound signals towards an anatomical object 105 and receives echo signals reflected from the object 105 back to the transducer array 112. The transducer array 112 may include acoustic elements arranged in a one-dimensional (1D) array or in a two-dimensional (2D) array. The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component.

The processing component 116 is coupled to the beamformer 114. The processing component 116 generates image data from the image signals. The processing component 116 may be implemented as a combination of software components and hardware components. In an embodiment, the processing component 116 may be implemented on a field programmable gate array (FPGA) and may include programmable state machines to control the processing and conversion of the image signals to the image data. For example, the processing component 116 may perform filtering and/or quadrature demodulation to condition the image signals. The processing component 116 may perform analytic detection on the filtered signals. The display 117 is coupled to the processing component 116. The display 132 may be a screen or any suitable display integral with the housing of the probe 110. The display 117 may be configured to display the results of the analytic detection.

The communication interface 118 is coupled to the processing component 116. The communication interface 118 transmits the image signals to the host 130 via the communication link 120. At the host 130, the communication interface 136 may receive the image signals. The host 130 may be any suitable computing and display device, such as a workstation, a personal computer (PC), a laptop, a tablet, or a mobile phone. The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

The processing component 134 is coupled to the communication interface 136. The processing component 134 may be implemented as a combination of software components and hardware components. The processing component 134 may include a central processing unit (CPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to perform image processing and image analysis for various diagnostic modalities. The display 132 is coupled to the processing component 134. The display 132 may be a monitor or any suitable display. The display 132 is configured to display images and/or diagnostic results processed by the processing component 134.

The system 100 can be configured for dynamic AB detection. For example, the object 105 may correspond to a portion of a patient's body including at least a portion of the patient's lung. In one embodiment, the probe 110 transmits the image signals (e.g., the echo signals) received from the transducer array 112 to the host 130. The processing component 134 can detect dynamic ABs from ultrasound images and indicate a positive dynamic AB detection and a location of the detected dynamic AB or a negative dynamic AB detection on the display 132. The processing component 134 can identify dynamic ABs based on a variation of a number of bright spots or pixels across a number of image frames over time. Alternatively, the processing component 134 can identify dynamic ABs based on a temporal intensity variation of bright spots or pixels across a number of image frames over time. The processing component 134 can enhance the appearance or visibility of bronchial trees in ultrasound images. Mechanisms for detecting dynamic ABs and enhancing bronchial trees are described in greater detail herein. In another embodiment, the processing component 116 on the probe 110 can be configured to perform dynamic AB detection eliminating the need of a host. In such an embodiment, dynamic AB detection results can be displayed on the integral display 117.

One of the ultrasound imaging sign for identifying PN is the detection of a positive dynamic AB within a lung consolidation. An AB is a tubular outline of an airway visible under lung ultrasound imaging due to the filling of surrounding alveoli by fluid or inflammatory exudates. Some studies have shown that the combination of a lung consolidation with dynamic AB accounts for about 70 percent (%) of total PN cases in clinical practices.

Figure 2:
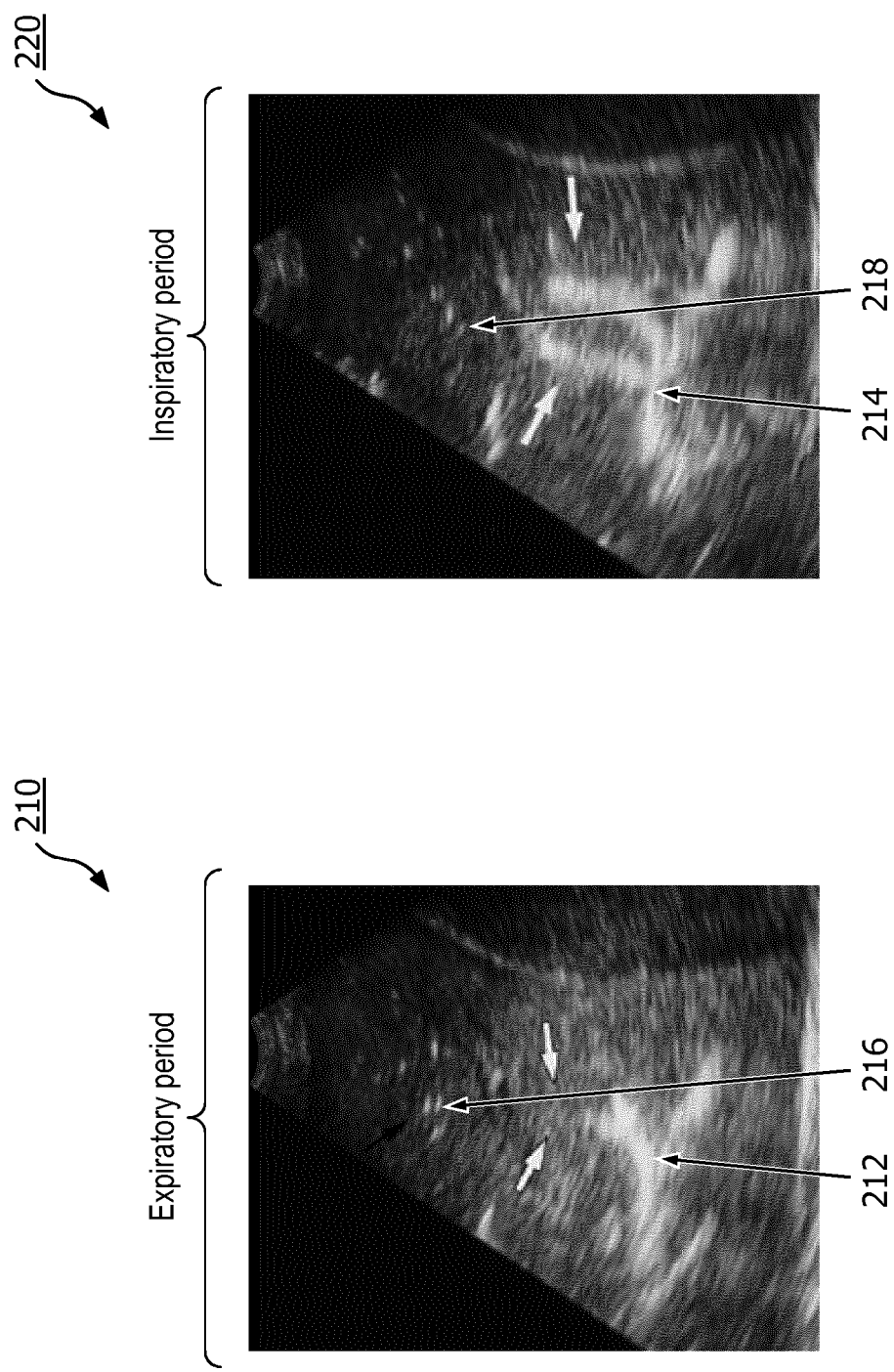
FIG. 2 illustrates the dynamics of ABs from an expiratory period to an inspiratory period, according to aspects of the present disclosure.

FIG. 2 illustrates the dynamics of ABs from an expiratory period to an inspiratory period, according to aspects of the present disclosure. In FIG. 2, the image 210 is acquired during an expiratory period of a patient and the image 220 is acquired during an inspiratory period of the patient. As shown in the image 210, ABs 212 appear as tubular bright structures. Similarly in the image 220, the ABs 214 appear as tubular bright structures. As can be observed, the appearance of ABs (e.g., bright structures) varies over time, for example, from the ABs 212 in the expiratory period to the ABs 214 in the inspiratory period. In addition, the images 210 and 220 show movements of punctiform ABs 216 (e.g., bright spots) to punctiform ABs 218.

Figure 3:
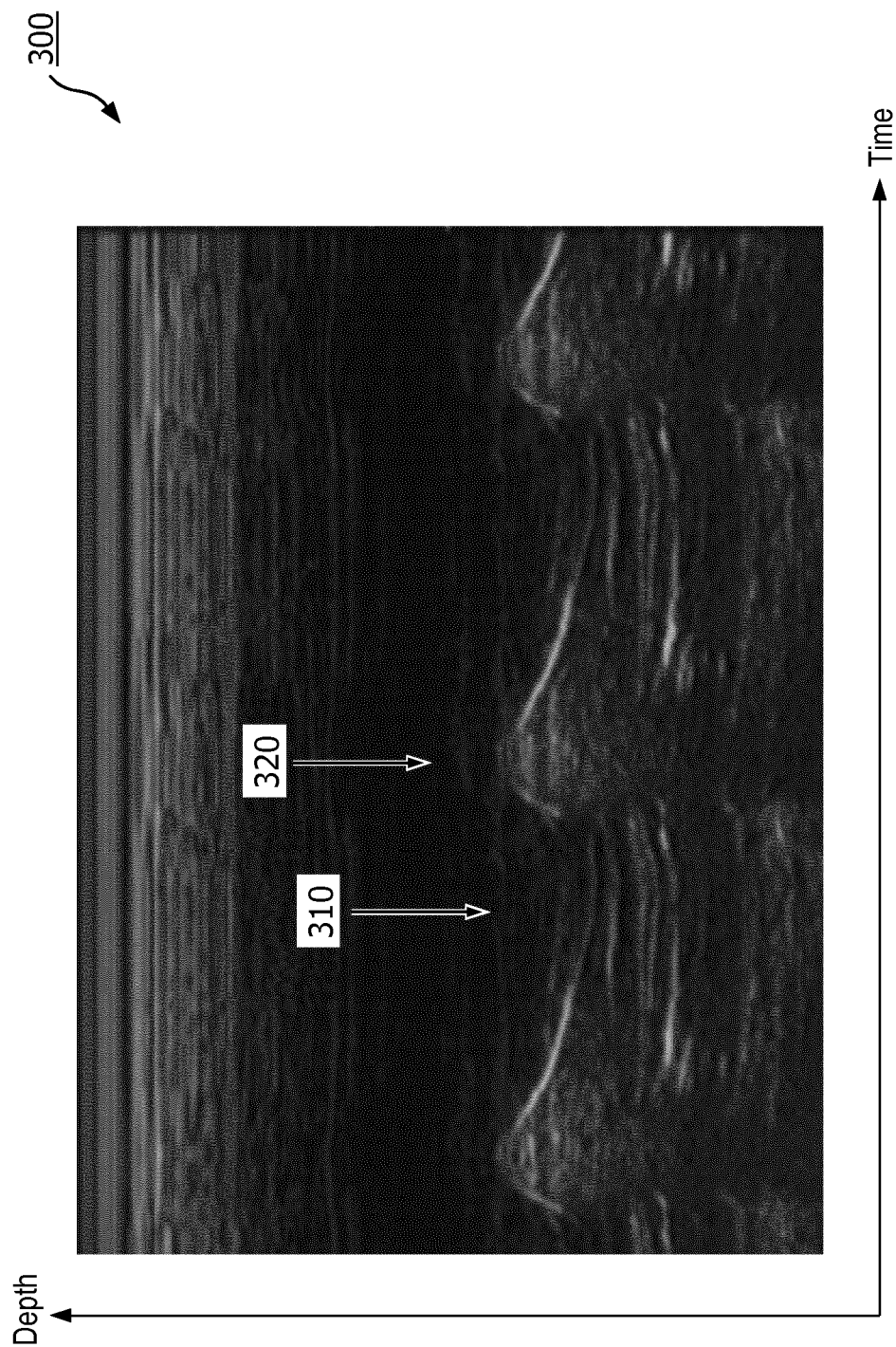
FIG. 3 illustrates the dynamics of ABs in an area of a lung consolidation over time, according to aspects of the present disclosure.

FIG. 3 illustrates the dynamics of ABs in an area of a lung consolidation over time, according to aspects of the present disclosure. In FIG. 3, the x-axis represents time in some constant units and the y-axis represents depths in some constant units. The image 300 illustrates a real-time ultrasound scan line as a function of time. For example, the transducer array 112 is used to generate one beam directed along a scan line towards an area within a lung consolidation and repeat at some time intervals. The image 300 shows the echo signals received from transducer array 112 corresponding to the emitted beam. In the image 300, the bright cyclic patterned lines show the movements or shift of ABs, such as the ABs 212, 214, 216, and 218, in a periodic manner. The cyclic or periodic pattern corresponds to the expiratory period 310 and inspiratory period 320 as marked in the image 300.

As can be seen in FIGS. 2 and 3, dynamic ABs can be detected based on intensity variations of pixels across image frames over one or more respiratory cycles. However, real-time visual identification of dynamic ABs may be difficult or unreliable due to the fast movements or motions of the dynamic ABs while the lung in the background of the ultrasound images may still be moving during respiration, where a respiratory cycle may span a duration of about 3 seconds to about 6 seconds. In addition, the clinician that performs the lung ultrasound imaging (e.g., at a POC-US) may not necessarily be trained for interpreting lung ultrasound images for dynamic AB detection.

Some studies conduct quantitative analysis for dynamic AB identification based on a measure of mean pixel intensities. While such quantitative analysis shows promising results (e.g., with a detection sensitivity of about 93%), the quantitative analysis requires expertise to identify and isolate regions corresponding to a patient's lung. In addition, the quantitative analysis approach may only perform well for a large area of lung consolidation and may miss detection of a small lung consolidation (e.g., extending less than about 1 centimeter (cm)) or PN at an early stage.

Figure 4:
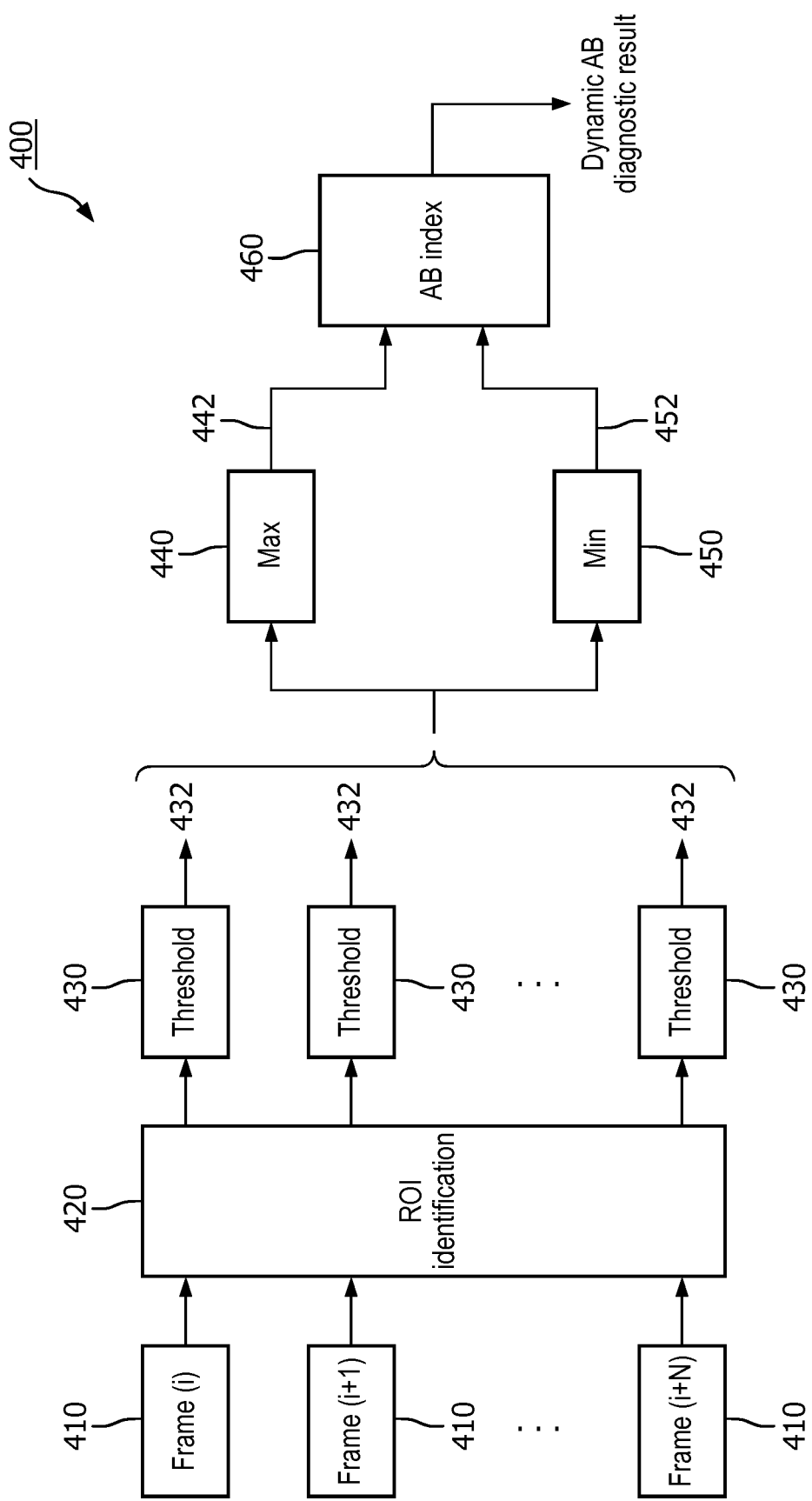
FIG. 4 is a schematic diagram illustrating a dynamic AB detection scheme, according to aspects of the present disclosure.

FIG. 4 is a schematic diagram illustrating an automatic dynamic AB detection scheme 400, according to aspects of the present disclosure. The scheme 400 can be employed by the system 100 for dynamic AB detection. Specifically, the scheme 400 can be implemented by the processing component 134 on the host 130 or the processing component 116 on the probe 110. In some embodiments, the implementation of the scheme 400 can be divided between the host 130 and the probe 110.

The scheme 400 begins with receiving a number of image frames 410. The image frames 410 may be generated by using the probe 110, where ultrasound signal energy is emitted from the transducer array 112 towards a patient's body (e.g., the object 105) and echo signals are received by the transducer array 112 forming the image frames 410. The probe 110 can be positioned on the patient's body to obtain an anterior chest view (e.g., from above the chest area) or a lateral chest view (e.g., from the side of the chest area) including at least some portions of the patient's lungs. Each image frame 410 may include a plurality of pixel values (e.g., amplitudes) representing pixel intensities of an image of the patient's body. The image frames 410 may be taken over a time period including at least one respiratory cycle (e.g., an expiratory period and an inspiratory period). The image frames 410 are shown as Frame(i) to Frame (i+N) representing images of the patient's body from a time instant (i) to a time instant (i+N), where i and N are positive integers.

The image frames 410 can include other portions of the patient's body in addition to the patient's lung. The scheme 400 can apply a region-of-interest (ROI) identification component 420 to the image frames 410 to identify portions of the image frames corresponding to the patient's lung for subsequent processing. One approach to identifying an area of a lung is based on a pleural line identification. A pleural line may appear as a bright line in an ultrasound image (shown in FIG. 5) and the region below the pleural line may correspond to the lung. After identifying the portions corresponding to the patient's lung, the ROI identification component 420 can identify an ROI in an area of the lung with a potential lung consolidation for the subsequent processing. For example, the ROI identification component 420 may perform bulk background motion detection using block-matching on a frame-by-frame basis, for example, based correlations across the image frames 410.

After identifying the ROI, the ROI identification component 420 may use the initial frame (e.g., Frame (i)) as an anchoring frame to align or register subsequent image frames 410 (e.g., Frame (i+1) to Frame (i+N)) to the initial image frame 410 based on the background motion information for subsequent operations described below. The alignment or registration allows the operations to be performed on the same portion of the lung for each image frame 410.

After identifying the ROI, a threshold component 430 can be applied to each image frame 410. The threshold component 430 determines the number of pixels in the ROI of a corresponding image frame 410 that are above a predetermined threshold. The number of pixels above the threshold may be represented by a count value 432. The pixels that are above the threshold may correspond to bright spots as shown in the ABs 212, 214, 216, and 218. The predetermined threshold may be configured to any suitable value depending on the dynamic range of the pixel values and the amplitude and/or pixel distribution in the ROI. In an embodiment, the dynamic range of the pixel intensity values may be configured to be between about 0 and about 255. In such an embodiment, the threshold may be configured to a value between about 40 to about 80.

After determining the number of bright pixels in each image frame 410, a maximum component 440 and a minimum component 450 can be applied to the count values 432. The maximum component 440 determines a maximum value 442 of the count values across the image frames 410. The minimum component 450 determines a minimum value 452 of the count values 432 across the image frames 410. In an embodiment, the maximum value 442 and the minimum value 452 can be normalized such that the maximum value 442 has a value of one.

After determining the maximum value 442 and the minimum value 452, an AB index component 460 can be applied to determine a dynamic AB diagnostic result. As described above, dynamic ABs are shown as bright structures (e.g., the ABs 212 and 214) or bright spots (e.g., the ABs 216 and 218) varying over time. The AB index component 460 identifies the dynamics of the ABs by computing a ratio between the maximum value 442 and the minimum value 452. The ratio may be referred to as an AB index. For example, the AB index component 460 may compare the ratio to a predetermined threshold. When there is a large variation between the maximum value 442 and the minimum value 452, a dynamic AB condition may be positive. Conversely, when there is a small variation between the maximum value 442 and the minimum value 452, a dynamic AB condition may be negative and a static AB condition may be present. The presence of a dynamic AB condition may indicate a high likelihood of PN, while the presence of a static AB condition may indicate a high likelihood of atelectasis (e.g., lung collapse without infection) or other lung diseases. The dynamic AB diagnostic result can be displayed on the display 132 and/or the display 117. In addition, the result may indicate the location of the dynamic AB condition in the lung.

Figure 5:
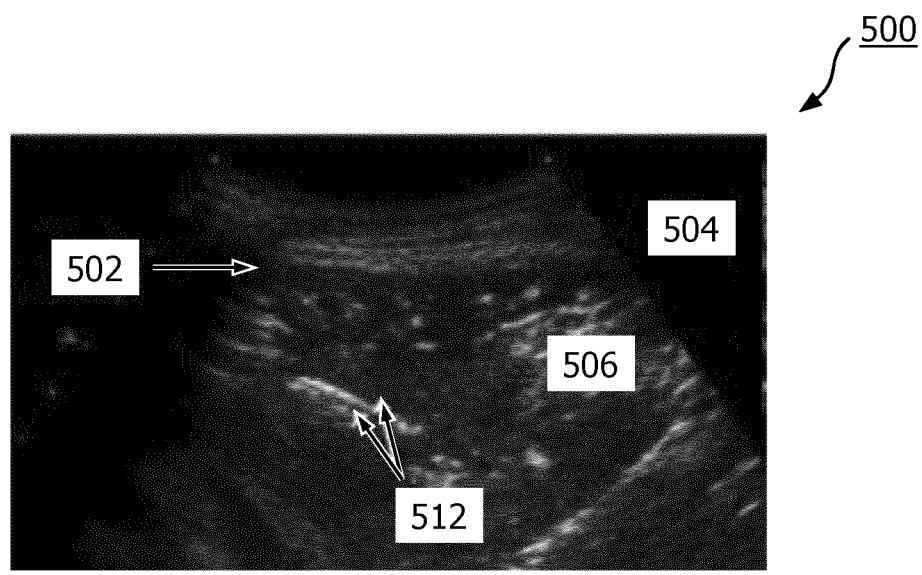
FIG. 5 is an image frame illustrating dynamic ABs, according to aspects of the present disclosure.

FIG. 5 is an ultrasound image 500 illustrating dynamic ABs, according to aspects of the present disclosure. The image 500 may be acquired using the system 100. The image 500 may represent an image of a patient's body (e.g., the object 105) including an area of a lung. The image 500 illustrates the presence of ABs 512 and lung consolidation 506 in an area of the patient's lung. As marked in the image 500, a pleural interface 502 or pleural boundary appears as a bright line across the image 500. The area below the pleural interface 502 corresponds to the patient's lung. The area above the pleural interface 510 corresponds to the patient's chest wall 504.

Figure 6:
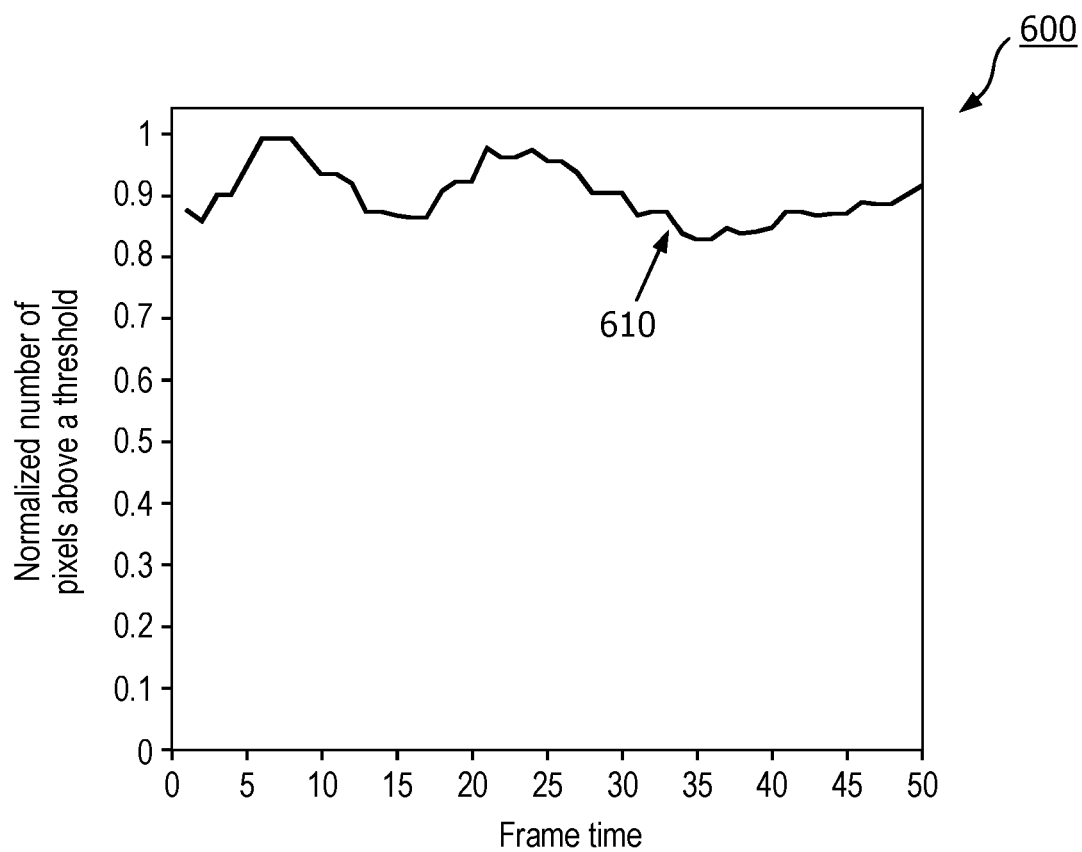
FIG. 6 is a graph illustrating variations of a number of bright pixels across a number of image frames over time in the presences of dynamic ABs, according to aspects of the present disclosure.

FIG. 6 is a graph 600 illustrating variations of a number of bright pixels across a number of image frames over time in the presences of dynamic ABs, according to aspects of the present disclosure. The x-axis represents frame number. The y-axis represents normalized number of pixels in an ROI within image frames that are above a predetermined intensity threshold. The graph 600 is generated using the scheme 400. The plot 610 shows the variations of the number of pixels above the threshold (e.g., the count values 432 in a normalized form) across a number of image frames (e.g., the image frames 410) over time in the region of the dynamic ABs 512 shown in the image 500. As can be seen, the plot 610 varies between about 0.84 to about 1. The large difference between the minimum (e.g., 0.84) and the maximum (e.g., 1) and the cyclic patterns observed in the plot 610 may indicate the presence of a dynamic AB condition. The cyclic or periodic patterns may correspond to respiratory cycles of the patient.

Figure 7:
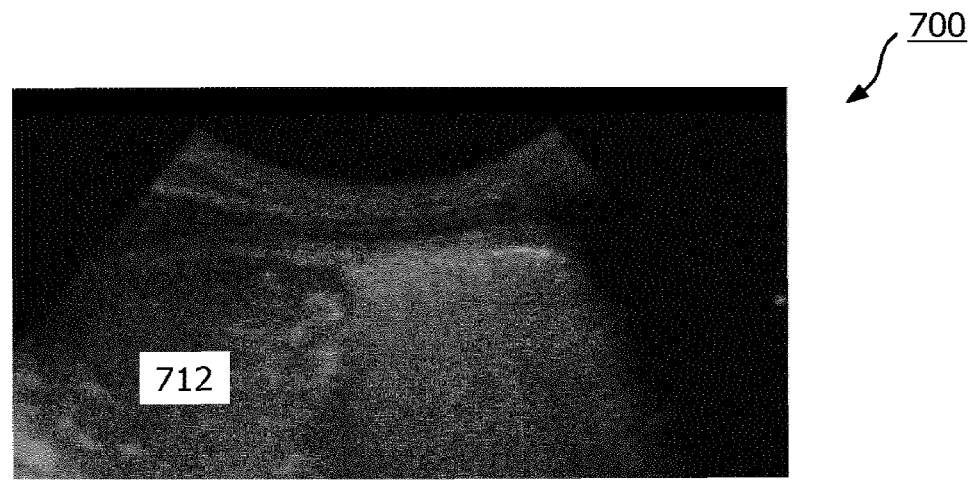
FIG. 7 is an image frame illustrating static ABs, according to aspects of the present disclosure.

FIG. 7 is an ultrasound image 700 illustrating static ABs, according to aspects of the present disclosure. The image 700 may be acquired using the system 100. The image 700 may represent an image of a patient's body (e.g., the object 105) including an area of a lung. The image 700 illustrates the presence of static ABs 712 in an area of the patient's lung.

Figure 8:
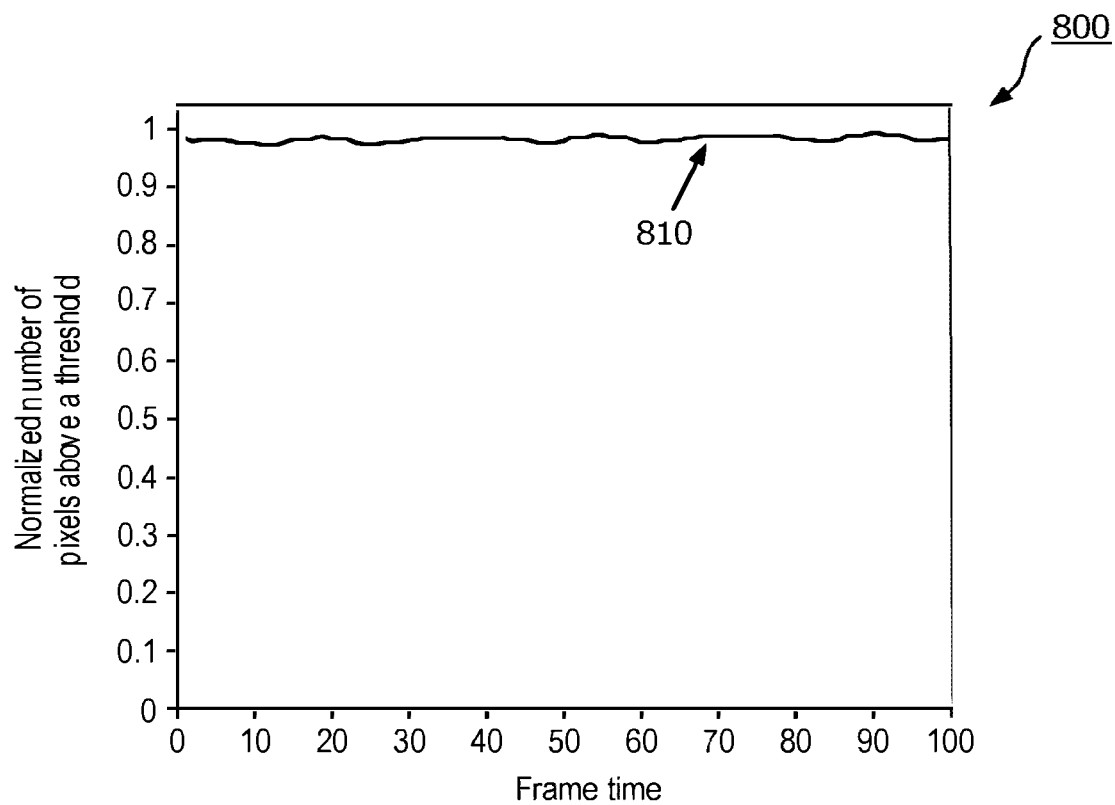
FIG. 8 is a graph illustrating variations of a number of bright pixels across a number of image frames over time in the absence of dynamic ABs, according to aspects of the present disclosure.

FIG. 8 is a graph 800 illustrating variations of a number of bright pixels across a number of image frames over time in the absence of dynamic ABs, according to aspects of the present disclosure. The x-axis represents frame number. The y-axis represents normalized number of pixels in an ROI within image frames that are above a predetermined intensity threshold. The graph 800 is generated using the scheme 400. The plot 810 shows the variations of the number of pixels above the threshold (e.g., the count values 432 in a normalized form) across a number of image frames (e.g., the image frames 410) over time in the region of the static ABs 712 of the image 700. As can be seen, the plot 810 is relatively static varying between about 0.987 to about 1. The small difference between the minimum (e.g., 0.987) and the maximum (e.g., 1) and the relatively static pattern observed in the plot 810 may indicate the presence of a static AB condition (e.g., an atelectasis condition).

Figure 9:
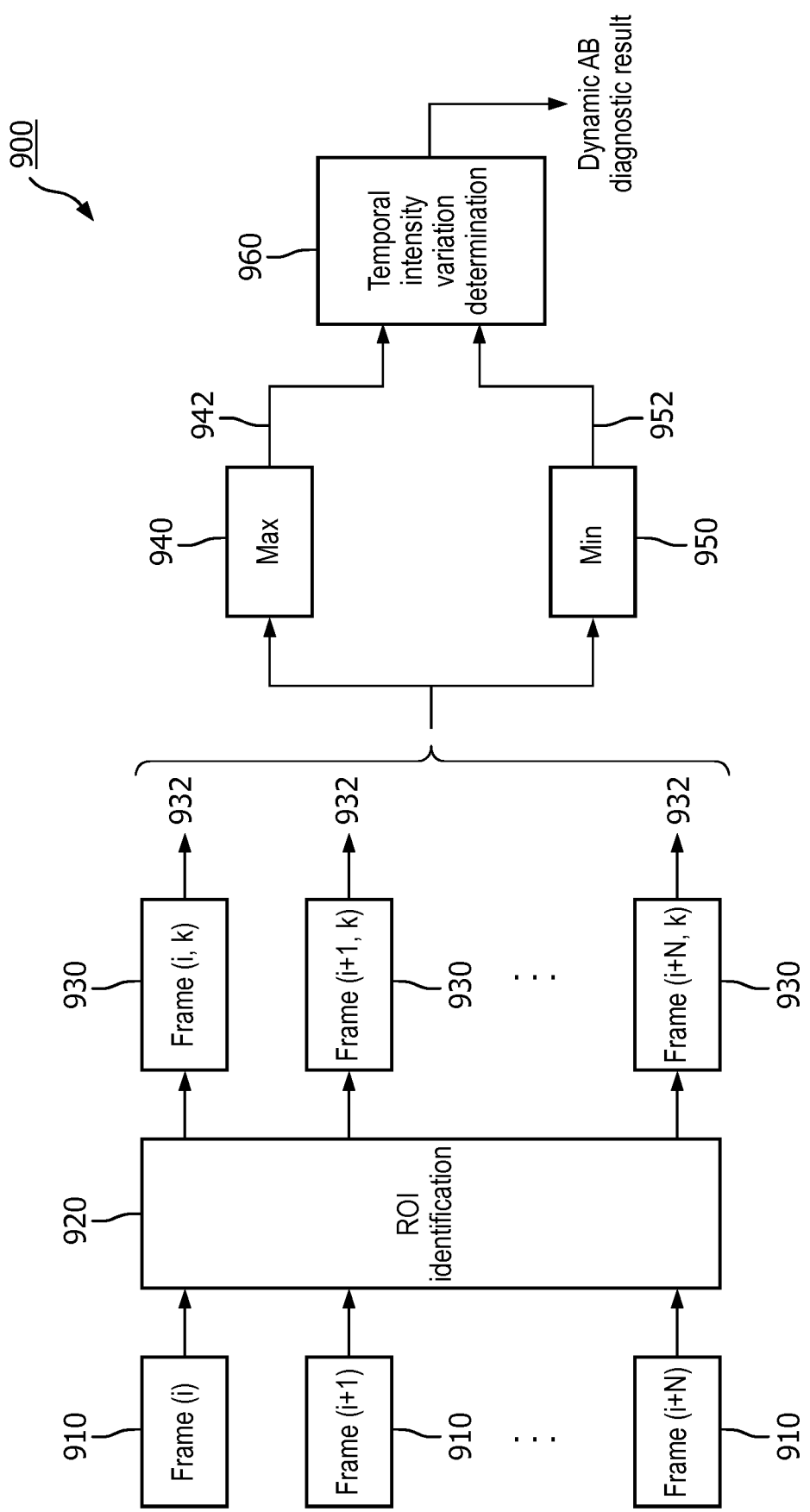
FIG. 9 is a schematic diagram illustrating a dynamic AB detection scheme, according to aspects of the present disclosure.

FIG. 9 is a schematic diagram illustrating a dynamic AB detection scheme 900, according to aspects of the present disclosure. The scheme 900 can be employed by the system 100 for dynamic AB detection. Specifically, the scheme 900 can be implemented by the processing component 134 on the host 130 or the processing component 116 on the probe 110. In some embodiments, the implementation of the scheme 900 can be divided between the host 130 and the probe 110.

The scheme 900 begins with receiving a number of image frames 910 similar to the image frames 410. For example, each image frame 910 includes pixel intensity values representing an image of a patient's body including at least a portion of the patient's lung. The scheme 900 can apply an ROI identification component 920 to the image frames 910. The ROI identification component 920 may be substantially similar to the ROI identification component 420. The ROI identification component 920 may identify a subset of data or pixels from the image frames 910 for dynamic AB condition determination. The identification may include selecting one or more pixel values from each image frame 910 corresponding to the same portion of the patient's lung around a lung consolidation. The ROI identification component 920 may output image data subsets 930 including pixels within the ROI. The subsets 930 are shown as Frame (i, k) to Frame (i+N, k) representing a subset k within Frame (i) to a subset k within Frame (i+1), respectively. When each subset 930 includes one pixel value, the pixel value is represented by an intensity value 932. When each subset 930 includes more than one pixel values, a spatial filter may be applied to each subset 930 to produce an average intensity value 932.

After identifying the subsets 930, a maximum component 940 and a minimum component 950 can be applied to the intensity values 932. The maximum component 940 determines a maximum value 942 of the intensity values 932. The minimum component 950 determines a minimum value 952 of the intensity values 932. In an embodiment, the maximum value 942 and the minimum value 952 can be normalized such that the maximum value 942 has a value of 1. In some embodiments, a temporal filter (e.g., a smoothing filter) can be applied to the subsets 930, for example, to obtain an average value over a number of frames, before determining the maximum value 942 and the minimum value 952.

After determining the maximum value 942 and the minimum value 952, a temporal intensity variation determination component 960 can be applied to determine a dynamic AB diagnostic result. The temporal intensity variation determination component 960 determines a temporal intensity variation across the subsets 930 over time. The temporal intensity variation determination component 960 can determine a ratio between the maximum value 942 and the minimum value 952. The temporal intensity variation determination component 960 can compare the ratio to a predetermined threshold and determine whether a dynamic AB condition is present based on the threshold comparison. Similar to the scheme 400, a large variation between the maximum value 942 and the minimum value 952 is indicative of a positive dynamic AB condition and a small variation between the maximum value 942 and the minimum value 952 is indicative of a negative dynamic AB condition.

Figure 10:
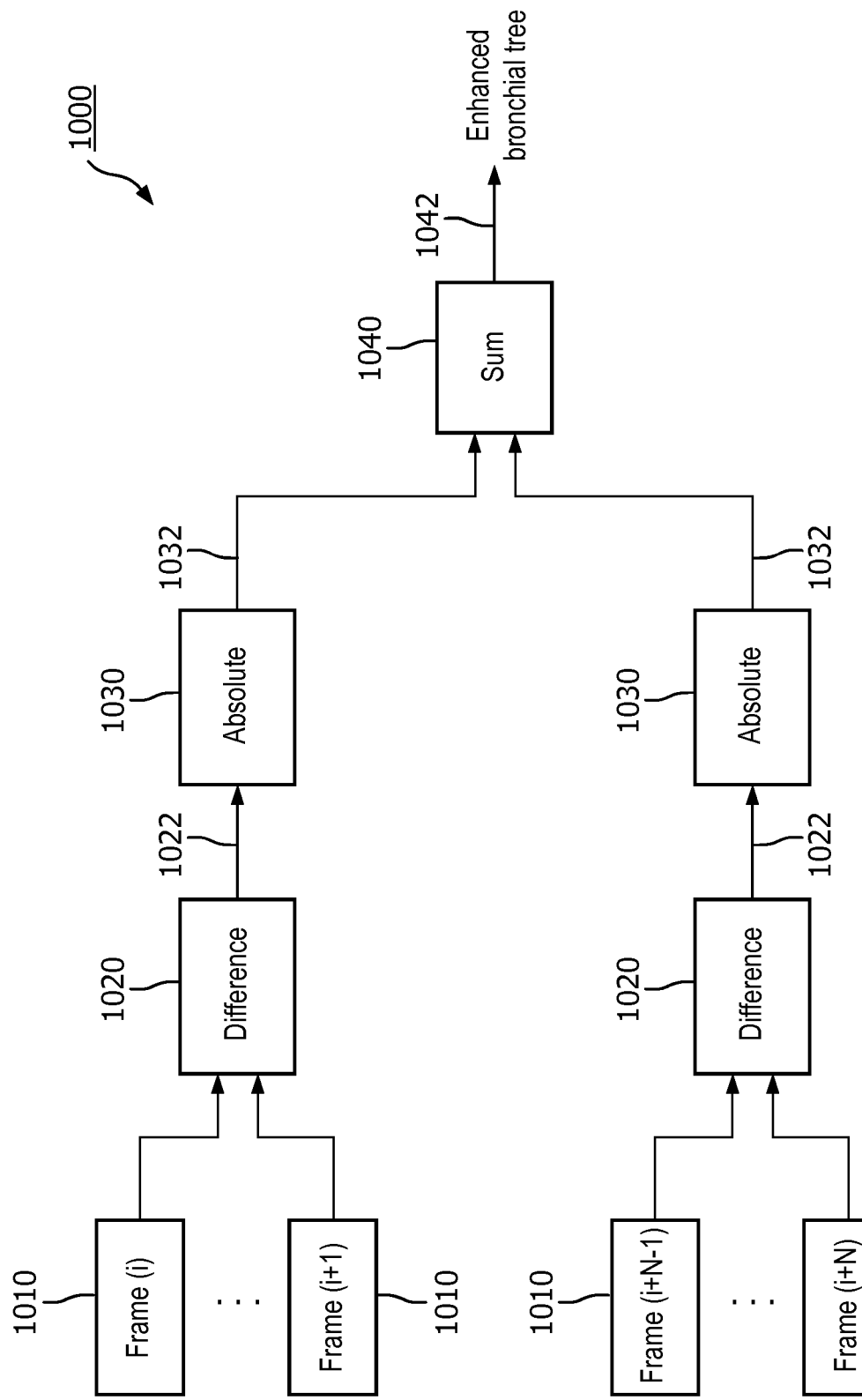
FIG. 10 is a schematic diagram illustrating a bronchial tree enhancement scheme, according to aspects of the present disclosure.

FIG. 10 is a schematic diagram illustrating a bronchial tree enhancement scheme 1000, according to aspects of the present disclosure. The scheme 1000 can be employed by the system 100 to enhance bronchial trees within a lung consolidation in lung ultrasound images for dynamic AB diagnosis. Specifically, the scheme 1000 can be implemented by the processing component 134 on the host 130.

The scheme 1000 begins with receiving a number of image frames 1010 similar to the image frames 410 and 910. For example, each image frame 1010 includes pixel intensity values representing an image of a patient's body including at least a portion of the patient's lung. The scheme 1000 applies a difference component 1020 to each pair of adjacent or consecutive image frames 1010 (e.g., Frame (i) and Frame (i+1)). The difference component 1020 computes a difference between the adjacent image frames 1010 to produce a differential image frame 1022. For example, the difference component 1020 subtracts the pixel values in the Frame (i) by the pixel values in the Frame (i+1) on a pixel-by-pixel basis. The pixel values of the Frame (i) and the pixel values of the Frame (i+1) correspond to the same sub-portion of the patient's lung.

An absolute component 1030 can be applied to the pixel values in the differential image frames 1022 to produce differential image frames 1032 with absolute difference pixel values. Subsequently, a sum component 1040 can be applied to accumulate the differential image frames 1032 to produce an accumulated image frame 1042. For example, the sum component 1040 sums the pixel values of the differential image frames 1032 on a pixel-by-pixel basis. When the image frames 1010 include a bronchial tree, the appearance or visibility of the bronchial tree may be enhanced in the accumulated image frame 1042 (shown in FIG. 11D below). The detection of the bronchial tree indicates a positive dynamic AB condition.

Figure 11B:
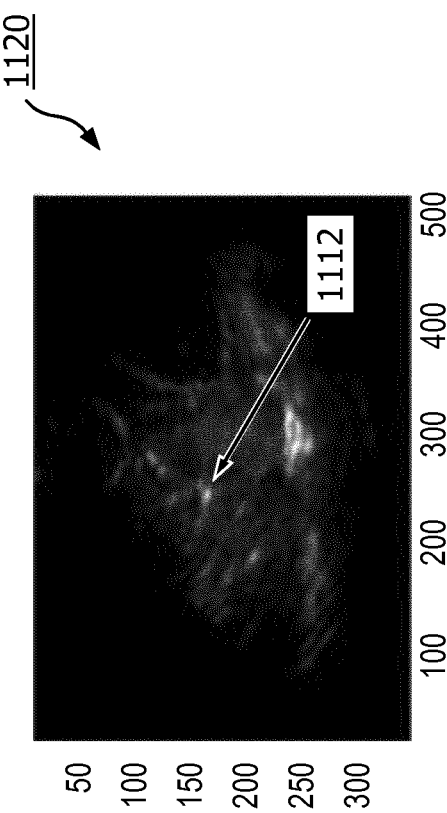
FIG. 11B is an image frame illustrating a bronchial tree at another time instant, according to aspects of the present disclosure.
Figure 11C:
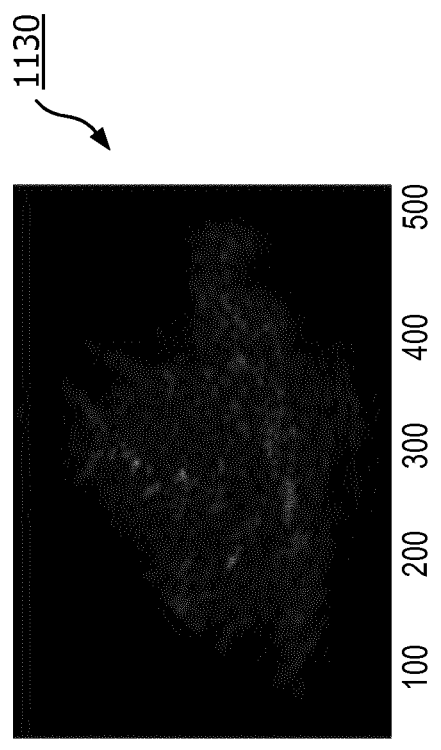
FIG. 11C is a differential image frame illustrating a difference between a pair of consecutive image frames including a bronchial tree, according to aspects of the present disclosure.
Figure 11A:
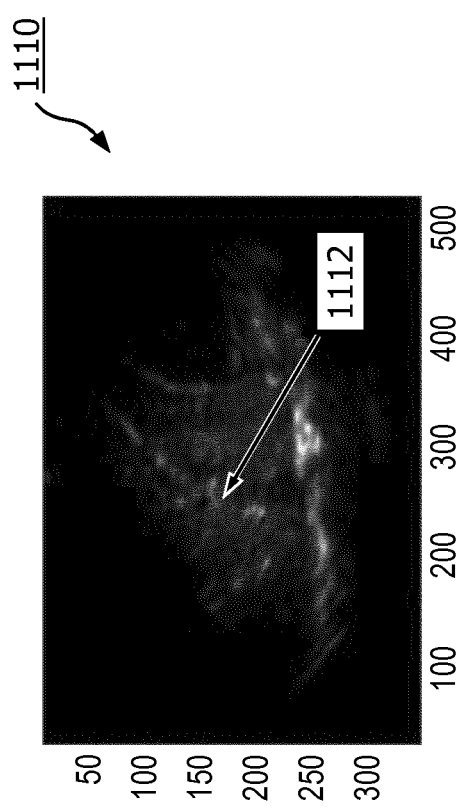
FIG. 11A is an image frame illustrating a bronchial tree at a time instant, according to aspects of the present disclosure.

FIGS. 11A-11D illustrates various image frames corresponding to various stages in the scheme 1000 described above with respect to FIG. 10. For example, the scheme 1000 is applied to eighty sequential ultrasound image frames, represented by Frame(1), Frame(2), . . . , Frame (80). FIG. 11A is an image frame 1110 illustrating a bronchial tree 1112 at a time instant, according to aspects of the present disclosure. The image frame 1110 may be similar to the image frames 410, 910, and 1010. The image frame 1110 may represent a first image frame (e.g., Frame (1)) of the eighty sequential image frames. As shown, the bright Y-shaped branching structure in the middle portion of the image frame 1110 corresponds to the bronchial tree 1112 within a lung consolidation of a patient. The bright curved horizontal structure at the bottom of the image frame 1110 corresponds to the patient's spine.

FIG. 11B is an image frame 1120 illustrating a bronchial tree 1112 at another time instant, according to aspects of the present disclosure. For example, the image frame 1120 may represent the last image frame (e.g., Frame (80)) of the eight sequential image frames.

FIG. 11C is a differential image frame 1130 illustrating a difference between a pair of consecutive image frames including a bronchial tree 1112, according to aspects of the present disclosure. For example, the differential image frame 1130 may represent a differential image frame 1032 at the output of the absolute component 1030 in the scheme 1000. The differential image frame 1130 may be computed by subtracting Frame (80) from Frame (79) pixel by pixel.

Figure 11D:
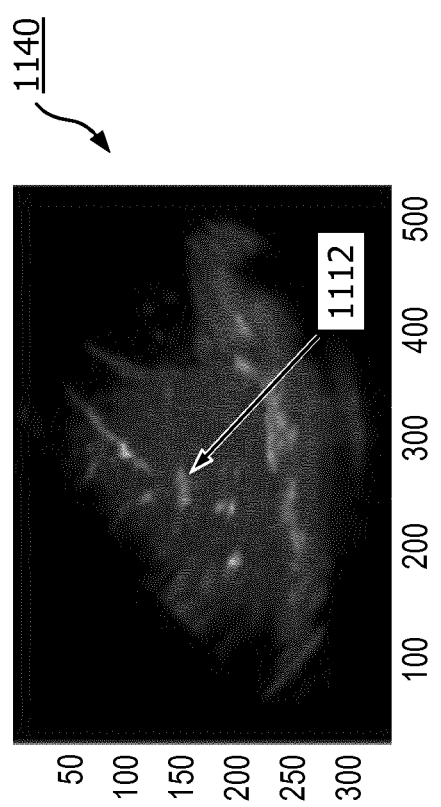
FIG. 11D is an accumulated image frame illustrating an enhanced bronchial tree, according to aspects of the present disclosure.

FIG. 11D is an accumulated image frame 1140 illustrating an enhanced bronchial tree 1112, according to aspects of the present disclosure. For example, the image frame 1140 may represent an accumulated image frame 1042 at the output of the sum component 1040 in the scheme 1000. Comparing the accumulated image frame 1140 to the originally acquired image frames 1110 and 1120, the appearance or visibility of the bronchial tree 1112 is enhanced in the accumulated image frame 1140.

Figure 12:
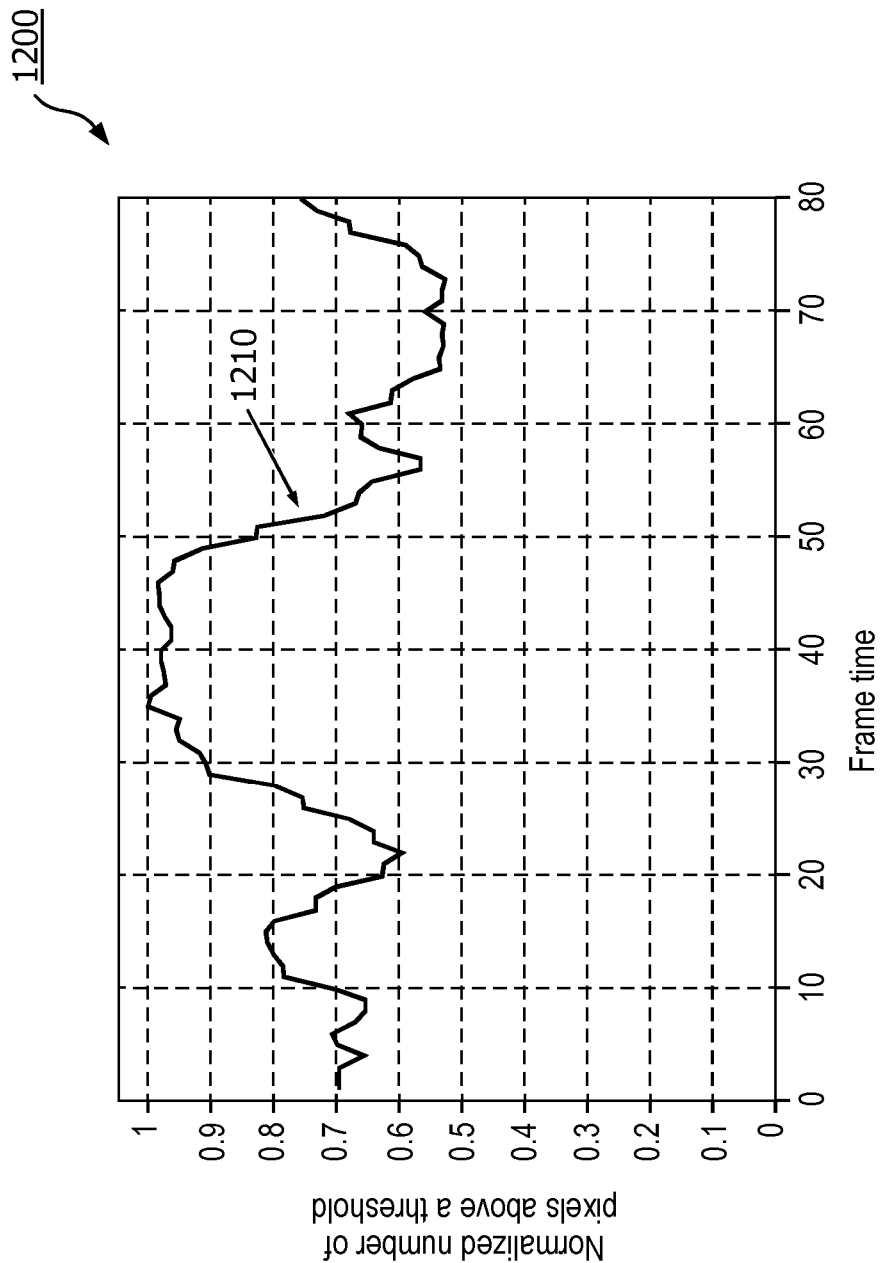
FIG. 12 is a graph illustrating variations of a number of bright spots across a number of image frames over time in the presence of dynamic ABs, according to aspects of the present disclosure.

FIG. 12 is a graph 1200 illustrating variations of a number of bright pixels across a number of image frames over time in the presence of dynamic ABs, according to aspects of the present disclosure. The x-axis represents frame number. The y-axis represents normalized number of pixels in an ROI within image frames that are above a predetermined intensity threshold. The graph 1200 is generated by applying the scheme 400 to the eight sequential image frames used for illustrating the scheme 1000 in FIG. 11. The plot 1210 shows variations of the normalized number of pixels above a predetermined threshold across a number of image frames (e.g., the image frames 1010) over time in the region of the bronchial tree 1112 shown in the image frames 1110 and 1120. As can be seen, the plot 1210 varies between about 0.53 to about 1. The large difference between the minimum (e.g., 0.53) and the maximum (e.g., 1) and the periodic waveform observed in the plot 1210 may indicate the presence of a dynamic AB condition.

Figure 13:
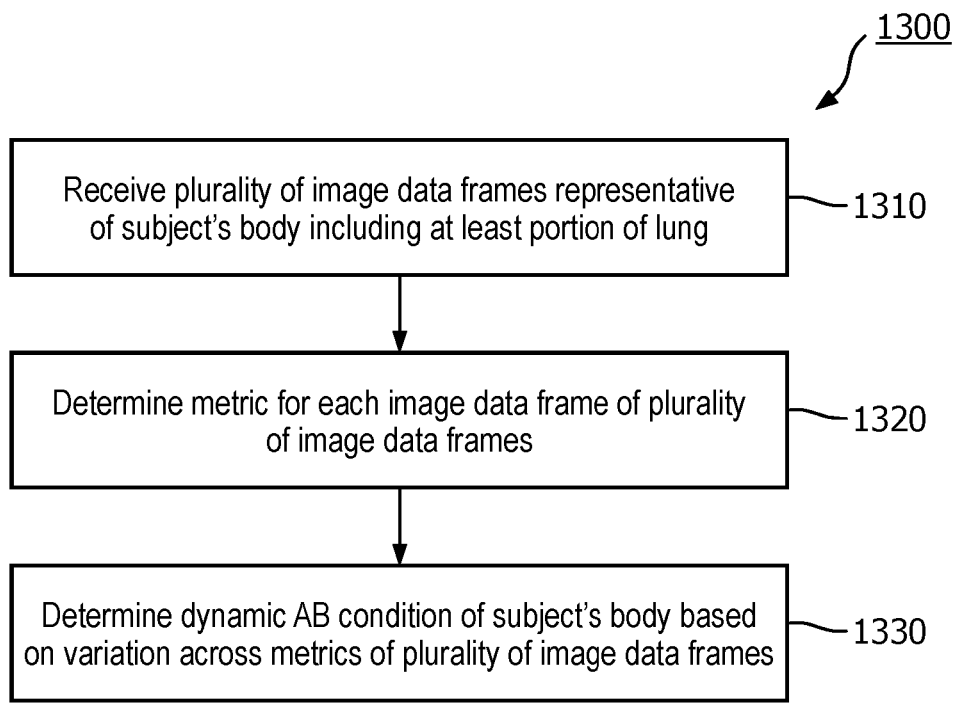
FIG. 13 is a flow diagram of a dynamic AB detection method, according to aspects of the present disclosure.

FIG. 13 is a flow diagram of a dynamic AB detection method 1300, according to aspects of the present disclosure. Steps of the method 1300 can be executed by a computing device (e.g., a processor, processing circuit, and/or other suitable component) of an ultrasound imaging probe, such as the probe 110, or a host such as the host 130. The method 1300 may employ similar mechanisms as in the scheme 400 as described with respect to FIG. 4. As illustrated, the method 1300 includes a number of enumerated steps, but embodiments of the method 1300 may include additional steps before, after, and in between the enumerated steps. In some embodiments, one or more of the enumerated steps may be omitted or performed in a different order.

At step 1310, the method 1300 includes receiving a plurality of image data frames (e.g., the image frames 410, 910, 1010, 1110, and 1120) representative of a subject's body (e.g., the object 105) including at least a portion of a lung. The subject's body may be a human body or an animal body.

At step 1320, the method 1300 includes determining a metric (e.g., the count values 432) for each image data frame of the plurality of image data frames, for example, using the threshold component 430.

At step 1330, the method 1300 includes determining a dynamic AB condition of the subject's body based on a variation across the metrics of the plurality of image data frames. For example, the maximum component 440 can be applied to the metrics to compute a maximum value (e.g., the maximum value 442) of the metrics and the minimum component 450 can be applied to the metrics to compute a minimum value (e.g., the minimum value 452) of the metrics. Subsequently, the AB index component 460 can be applied to compute a ratio between the maximum value and the minimum value and compare the ratio to a predetermine threshold. When the ratio satisfy the predetermine threshold, a positive dynamic AB condition may be present. When the ratio fails to satisfy the predetermined threshold, a dynamic AB condition may be absent.

Figure 14:
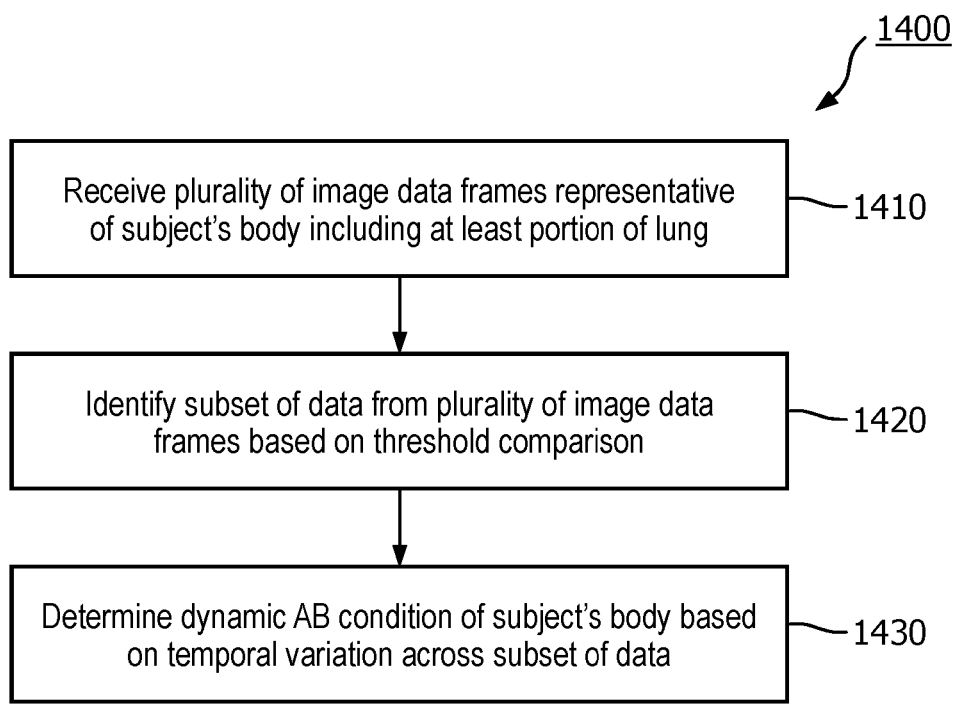
FIG. 14 is a flow diagram of a dynamic AB detection method, according to aspects of the present disclosure.

FIG. 14 is a flow diagram of a dynamic AB detection method 1400, according to aspects of the present disclosure. Steps of the method 1400 can be executed by a computing device (e.g., a processor, processing circuit, and/or other suitable component) of an ultrasound imaging probe, such as the probe 110, or a host such as the host 130. The method 1400 may employ similar mechanisms as in the scheme 900 as described with respect to FIG. 9. As illustrated, the method 1400 includes a number of enumerated steps, but embodiments of the method 1400 may include additional steps before, after, and in between the enumerated steps. In some embodiments, one or more of the enumerated steps may be omitted or performed in a different order.

At step 1410, the method 1400 includes receiving a plurality of image data frames (e.g., the image frames 410, 910, 1010, 1110, and 1120) representative of a subject's body (e.g., the object 105) including at least a portion of a lung. The subject's body may be a human body or an animal body.

At step 1420, the method 1400 includes identifying a subset of data (e.g., the subsets 930) from the plurality of image data frames based on a threshold comparison, for example, using the ROI identification component 920.

At step 1430, the method 1400 includes determining a dynamic AB condition of the subject's body based on a temporal variation across the subset of data. For example, the subset of data may include a portion (e.g., one or more pixel values) of each image data frame and a spatial filter can be applied to a corresponding portion of each image frame to determine a first value (e.g., the intensity values 932) for each image data frame. The maximum component 940 can be applied to the first values to compute a maximum value (e.g., the maximum value 942) of the first values and the minimum component 950 can be applied to the first values to compute a minimum value (e.g., the minimum value 952) of the first values. Subsequently, the temporal intensity variation determination component 960 can be applied to compute a ratio between the maximum value and the minimum value and compare the ratio to a predetermine threshold. When the ratio satisfy the predetermine threshold, a positive dynamic AB condition may be present. When the ratio fails to satisfy the predetermined threshold, a dynamic AB condition may be absent.

Figure 15:
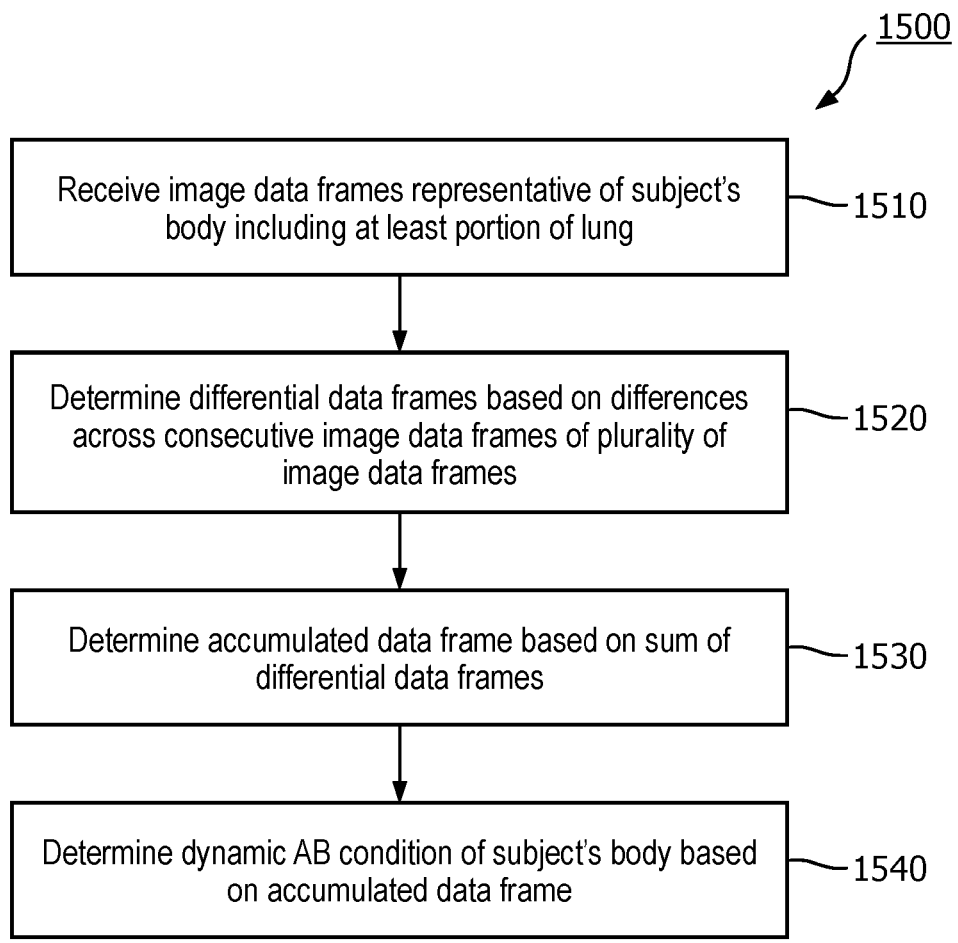
FIG. 15 is a flow diagram of a bronchial tree enhancement method, according to aspects of the present disclosure.

FIG. 15 is a flow diagram of a bronchial tree enhancement method 1500, according to aspects of the present disclosure. Steps of the method 1500 can be executed by a computing device (e.g., a processor, processing circuit, and/or other suitable component) of a host such as the host 130. The method 1500 may employ similar mechanisms as in the scheme 1000 as described with respect to FIG. 10. As illustrated, the method 1500 includes a number of enumerated steps, but embodiments of the method 1500 may include additional steps before, after, and in between the enumerated steps. In some embodiments, one or more of the enumerated steps may be omitted or performed in a different order.

At step 1510, the method 1500 includes receiving a plurality of image data frames (e.g., the image frames 410, 910, 1010, 1110, and 1120) representative of a subject's body (e.g., the object 105) including at least a portion of a lung. The subject's body may be a human body or an animal body.

At step 1520, the method 1500 includes determining differential data frames (e.g., the differential image frames 1032) based on differences across consecutive image data frames of the plurality of image data frames.

At step 1530, the method 1500 includes determining an accumulated data frame (e.g., the accumulated image frame 1042) based on a sum of the differential data frames.

At step 1540, the method 1500 includes determining a dynamic AB condition of the subject's body based on the accumulated data frame. For example, the accumulated data frame shows an enhanced appearance or visibility of the bronchial tree in a location within a lung consolidation. Thus, the determination may be on the observation of the bronchial tree.

Aspects of the present disclosure can provide several benefits. For example, the automatic detection of dynamic ABs without the need for a well-trained clinician to interpret ultrasound lung images allow point-of-care ultrasound (POC-US) imaging to be used for PN screening and diagnosis. The automatic dynamic AB detection can produce a diagnostic result in a short duration of time. Thus, PN examination time can be shortened when compared to a full chest PN examination. In addition, the disclosed embodiments provide a standardized testing protocol. The use of the standardized test protocol can produce more consistent diagnostic results than the subjective evaluations and analysis under different physicians and clinicians. The standardized test protocol can be carried out easily for screening and suitable for use in time critical situations (e.g., during an emergency). Further, the enhanced display of bronchial tree can assist a physician to identify a PN location quickly and easily. The disclosed embodiments are suitable for use with pediatric patients and/or pregnant women where radiation exposure is a concern.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an interface coupled to at least one of a transducer array and a beamformer, the interface to receive a plurality of image data frames representative of a subject's body including at least a portion of a lung, each image data frame of the plurality of image data frames including a plurality of pixel values representing pixel intensities of an image of the subject's body;

a processor in communication with the interface and configured to:

determine a count metric for each image data frame of the plurality of image data frames by counting a number of the plurality of pixel values in each image data frame that satisfies a threshold; and determine a dynamic air bronchogram (AB) condition of the subject's body based on a variation across the count metrics of the plurality of image data frames, wherein the dynamic AB condition is determined based on a calculated ratio between a maximum of the count metrics and a minimum of the count metrics.

2. The ultrasound imaging system of claim 1, wherein the plurality of image data frames represent images of the subject's body across a time period including at least one respiratory cycle.

3. The ultrasound imaging system of claim 1, wherein the processor is further configured to:

identify a region-of-interest (ROI) from the plurality of image data frames corresponding to the at least a portion of the lung; and determine the count metrics based on the ROI.

4. The ultrasound imaging system of claim 1, further comprising a display.

5. The ultrasound imaging system of claim 1, further comprising an ultrasound imaging probe comprising:

at least one of the transducer array and the beamformer;
the processor; and
a display.

6. An ultrasound imaging system, comprising:

an interface coupled to at least one of a transducer array and a beamformer, the interface to receive a plurality of image data frames representative of a subject's body including at least a portion of a lung across a time period, each image data frame of the plurality of image data frames including a plurality of pixel values representing pixel intensities of an image of the subject's body;

a processor in communication with the interface and configured to:

identify a subset of data from the plurality of image data frames by selecting one or more pixel values from each image data frame of the plurality of image data frames corresponding to a same sub-portion of the at least a portion of the lung;

determine an intensity metric for each image data frame from the subset of data; and determine a dynamic air bronchogram (AB) condition of the subject's body based on a temporal variation across the subset of data by comparing a maximum of the intensity metrics across the time period to a minimum of the intensity metrics across the time period, wherein the dynamic AB condition is determined based on a calculated ratio between a maximum of the intensity metrics and a minimum of the intensity metrics.

7. The ultrasound imaging system of claim 6, wherein the time period includes at least one respiratory cycle.

8. The ultrasound imaging system of claim 6, further comprising a display.

9. The ultrasound imaging system of claim 6, wherein the processor is configured to:

determine the dynamic AB condition based on a ratio between the maximum of the intensity metrics and the minimum of the of the intensity metrics.

10. The ultrasound imaging system of claim 9, wherein the processor is configured to apply a filter across the intensity metrics prior to the determining the dynamic AB condition.

* * * * *